United States Patent [19]
Gardineer et al.

[11] 4,282,880
[45] Aug. 11, 1981

[54] WATER CIRCULATION AND MAINTENANCE SYSTEM FOR AN ULTRASOUND MAMMARY SCANNING APPARATUS

[75] Inventors: Bayard G. Gardineer, Skillman; James A. Heringes, Dayton; Paul Mandel, Edison, all of N.J.

[73] Assignee: Technicare Corporation, Solon, Ohio

[21] Appl. No.: 129,813

[22] Filed: Mar. 12, 1980

[51] Int. Cl.³ .................................................. A61B 10/00
[52] U.S. Cl. ........................................................ 128/660
[58] Field of Search .............................. 128/660–663; 73/618–626, 644; 250/451, 456; 4/487, 489; 269/322–328

[56] References Cited

U.S. PATENT DOCUMENTS

| | | | |
|---|---|---|---|
| 3,404,678 | 10/1968 | Von Ardenne | 128/369 |
| 3,963,933 | 6/1976 | Henkes, Jr. | 250/456 |
| 4,001,899 | 1/1977 | Mathis | 4/489 X |
| 4,087,870 | 5/1978 | Palmer, Jr. | 4/487 X |
| 4,149,281 | 4/1979 | Bob et al. | 4/487 X |
| 4,167,180 | 9/1979 | Kossoff | 128/660 |
| 4,185,333 | 1/1980 | Ortega | 4/489 X |
| 4,222,274 | 9/1980 | Johnson | 128/660 X |
| 4,233,988 | 11/1980 | Dick et al. | 128/660 |

FOREIGN PATENT DOCUMENTS 2919995 11/1979 Fed. Rep. of Germany ............ 128/660

*Primary Examiner*—Francis J. Jaworski
*Attorney, Agent, or Firm*—Donal B. Tobin

[57] ABSTRACT

A water conditioning system for maintaining and conditioning the water used in an ultrasound imaging system especially adapted to perform diagnosis of the human breast. The system includes a cabinet enclosing a main tank which contains an ultrasound transducer and associated focusing lens submerged in water. The main tank has associated with it a main reservoir. A second quantity of water which is adapted to receive the patient's breast is contained in a flexible bag having an open end supported adjacent the patient and having a closed end draped into engagement with the water in the pool and the water in the tank. The suspension pool also has a reservoir associated with it. The main tank and the suspension pool each have separate but interdependent fluid circulation circuits for conditioning the water in the tank and the suspension pool to provide a good transmission medium by filtering heating purifying and monitoring the water level of the water in the tank and in the suspension pool.

22 Claims, 6 Drawing Figures

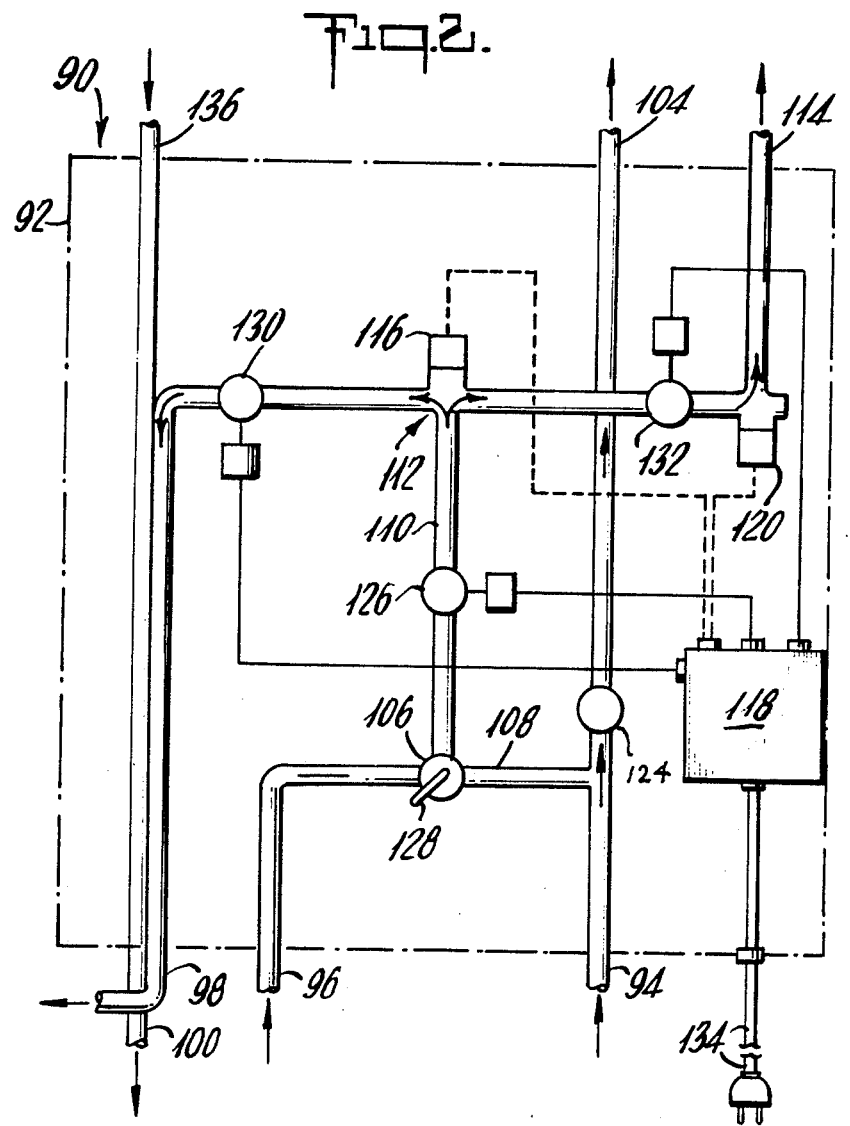

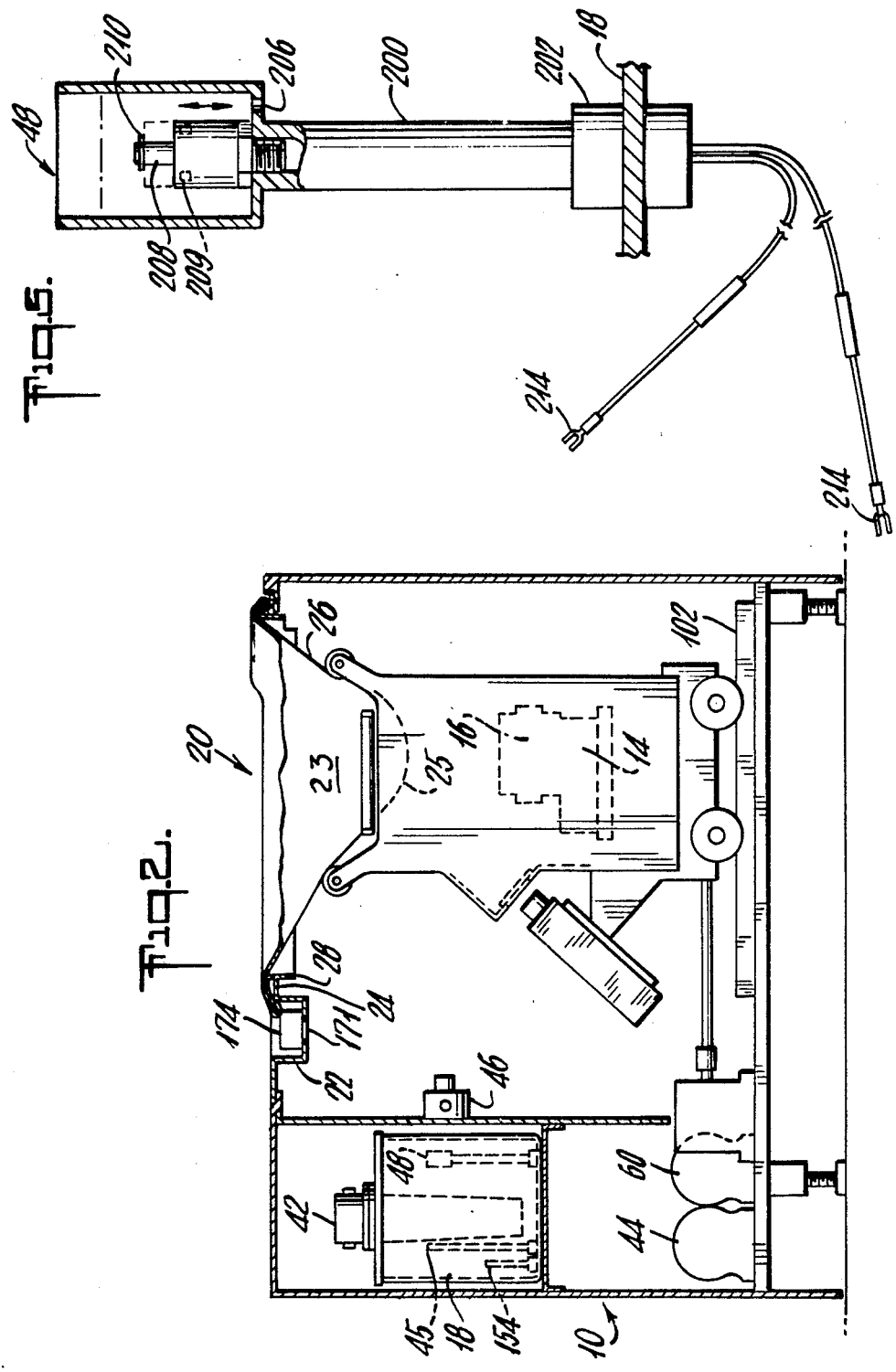

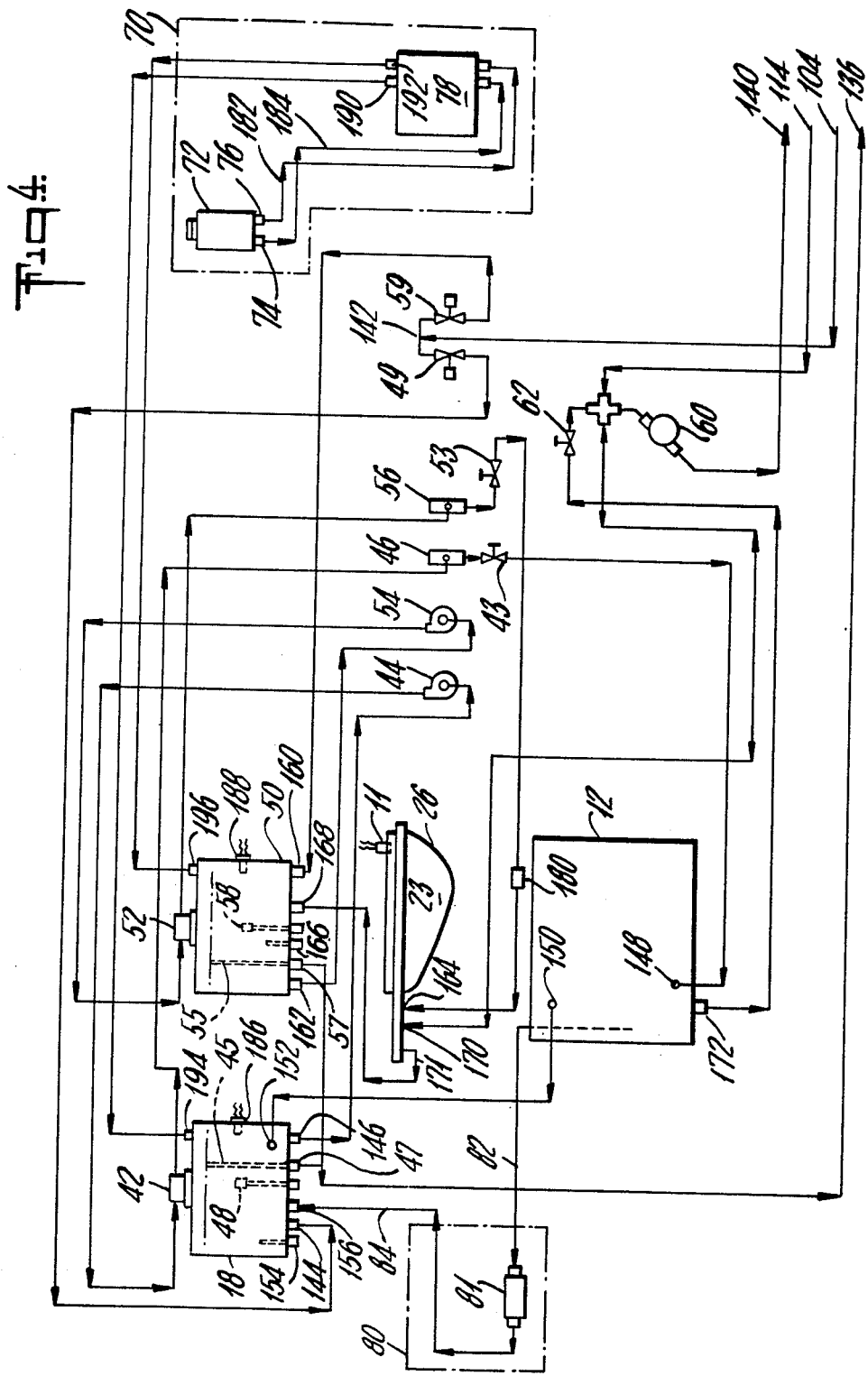

WATER CIRCULATION AND MAINTENANCE SYSTEM FOR AN ULTRASOUND MAMMARY SCANNING APPARATUS

FIELD OF THE INVENTION

This invention relates to ultrasound imaging systems especially adapted to perform diagnostic and screening imaging of the human breast and more particularly to a water circulation system for maintaining and conditioning the water used in the system.

BACKGROUND OF THE INVENTION

Ultrasonic imaging has rapidly become a preferred modality for the non-invasive investigation of human tissues. Its non-ionizing character, moderate requirements in terms of signal processing and computation support, compactness, and continuing progress in image all favor the use of ultrasound whenever conditions permit. Thus, with the exception of body areas which are subject to uncontrolled multiple reflections (e.g. in the skull) and areas which fundamentally possess poor sonic transmission characteristics (e.g. the lungs), most areas of the body have been successfully made the subject of ultrasound diagnosis or screening. Some systems are multipurpose in essence, such as real time or B-scan body scanners and fetal monitors, while others are highly specialized, such as pulsed Doppler carotid imagers and flow monitors.

Recently, scientific and clinical data have been produced which provide strong indication of the efficacy of ultrasound scanning and imaging to screen, detect, and diagnose lesions in the human breast. In particular, it appears that appropriately directed and controlled B-scan images of a human breast permit detection of lesions in the 1 to 2 millimeter range and discrimination of malignancies in the 5 millimeter range based solely on ultrasound image. Further, such screening appears feasible at statistical levels of confidence comparable to those achieved through utilization of ionizing radiation (i.e., X-ray mammography). Such efficacy, together with ultrasound's apparent hazard-free nature, makes ultrasound a likely preferred mordality for large scale screening programs for early detection of breast cancer.

Ultrasonic diagnosis of the human body using large aperture pulse echo ultrasound imaging techniques have been described in, for example, U.S. Pat. Nos. 4,131,021 and 4,131,022 to Mezrich et al. Accordingly, such devices use a scanning transducer and an associated sonic lens submerged in water. The subject is positioned on an examination table over the water enclosure. Sonic energy from the transducer is transmitted through the water, focused by the sonic lens through the examination table and into the patient. Echoes are transmitted back in similar fashion. When diagnosing the condition of the human breast, it has been found desirable to eliminate the examination table from the transmission path and to transmit ultrasonic energy directly to the breast.

In certain instances, it has been found desirable to examine the human breast while it is suspended in the water. Thus, it is necessary to condition the water used for the ultrasound transmission medium to remove sources of interference that could distort the ultrasound image. When conditioning may involve filtering particulate matter, deaerating the medium, maintaining proper water level, maintaining uniform temperature to eliminate thermal gradients, and inhibiting bacterial growth to minimize interference with the ultrasound transmissions. It is also important to maintain the temperature of the water at a proper level so that the patient experiences no discomfort when the breast is introduced into the water.

It is also desirable, from an aesthetic and sanitary point of view, to be able to change the water in which the breast is suspended after every patient, or at least after every several patients. A problem has existed which made frequent water changing impractical because the water had to be properly conditioned to be used as a transmission medium for the ultrasound system. Proper conditioning of the water, however, can take a significant amount of time so that previous breast scanning devices have had significant limitations on the ability to change water frequently. The present invention addresses these problems and provides an efficient, water maintenance system for an ultrasound mammary scanning apparatus.

SUMMARY OF THE INVENTION

The present invention relates to a water maintenance system for an ultrasound mammary scanning apparatus which is particularly adapted to examining the breast while it is suspended in water. A patient support platform is supported on top of a cabinet enclosing the ultrasound system which includes a transducer tank in which a scanning transducer and associated sonic lens are submerged in a fluid transmission medium, for example water. For convenience, the transmission medium will be identified as water throughout this application. However, those skilled in the art will appreciate that other transmission media can be used. The patient support platform includes an aperture in the surface against which the patient rests, which aperture is large enough to receive the patient's breast and surrounding axilla region. Fixed over a portion of the cabinet, under the platform, is a splash tray with a well aligned with the aperture in the support platform. A flexible membrane or bag is supported about the well by means of a frame mounted in the splash tray. The flexible bag contains a pool of water in which the patient's breast may be suspended during the diagnosis.

The bag is designed so that it drapes down from its support frame and contacts the surface of the water in the transducer tank so as to provide a continuous transmission medium through which the ultrasound transmissions may be propagated from the transducer tank to the suspension pool. The bag forms an interface between the water in the transducer tank and the suspension pool. It is, therefore, desirable that the bag be substantially ultrasonically transparent and that the properties of the water in the transducer tank and the suspension pool be substantially the same so that there is little refraction of or interference with the ultrasound waves as they propagate through the water in the tank and in the bag.

The present system uses two separate but interdependent systems for properly conditioning the water through which the ultrasound is transmitted. Two separate bodies of water are used, one in the main tank and one in the bag into which the patient's breast is suspended, so that the portion of the water which contacts the patient may be changed regularly for aesthetic and sanitary reasons without having to change the water in the entire system.

In order to provide a good transmission medium, it is desirable to maintain the water at the proper temperature, to filter particulate matter, to inhibit bacterial growth, maintain the correct water level, remove air bubbles from the water and from under the concave surface of the sonic lens. Temperature gradients, particulate matter, bacteria, air bubbles and varying water levels can all interfere with the transmission of the ultrasound waves from the transducer to the patient and, thus, these sources of interference must be controlled. The ability to control these sources of possible interference is facilitated by providing separate systems for the bag and the tank in which the water continuously circulates. Each body of water has a separate circulation system with its own reservoir, circulation pump, heater, filter, bacteria inhibitor and water level maintenance valve and associated sensors and valves. Continuously circulating the water in the two systems facilitates the removal of entrained air. A de-bubbling subsystem is used for removing bubbles from under the concave surface of the focusing lens. A separate subsystem is used for injecting metered amounts of a purifying solution, for example chlorine, into the water to control bacteria growth.

A thermostatic mixing assembly is connected between the plumbing at the facility where the scanning unit is installed and the water systems of the scanning system so that available water pressure and hot water may be used. The mixing assembly permits the bag to be filled directly with hot water at a controlled temperature from the facility boilers so that time for heating the water in the bag is reduced, and the water in the bag can, therefore, be changed more frequently. A discharge pump is provided for emptying the system.

Other features and advantages of the present invention will become apparent from the following detailed description of the preferred embodiments taken in conjunction with the following drawings.

BRIEF DESCRIPTION OF THE DRAWINGS

FIG. 2 shows a side elevation, partially in section, of the scanning cabinet showing certain internal components;

FIG. 3 shows a schematic representation of the fluid system for the thermostatic mixing assembly;

FIG. 4 shows a schematic diagram of the fluid circulation system; and

FIG. 5 shows a sectional elevation of a float valve used with the circulation system.

DETAILED DESCRIPTION OF THE PREFERRED EMBODIMENTS

Figure 1:
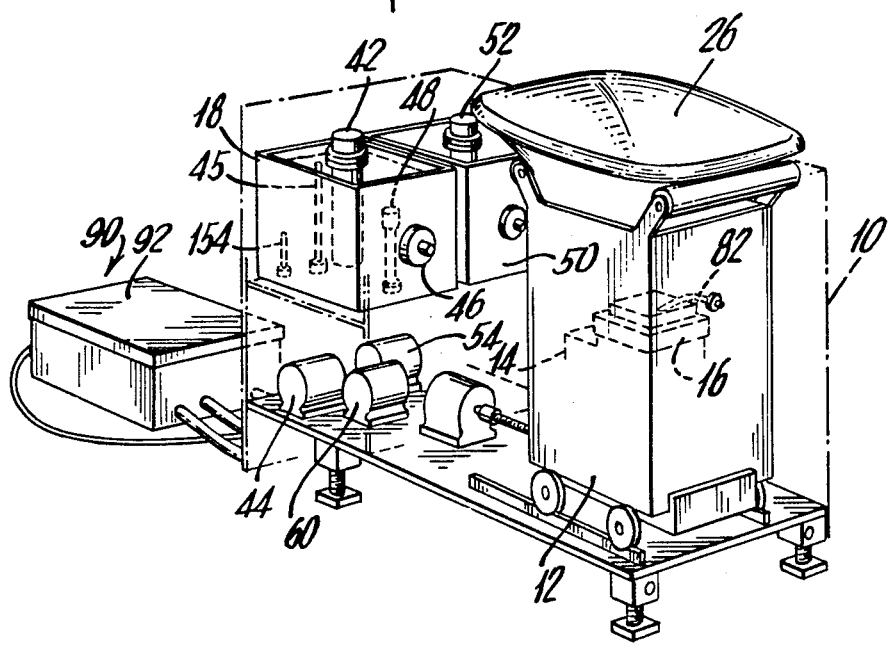
FIG. 1 shows a perspective view, partially in section, of the scanning tank cabinet and certain internal components.

The present invention relates to a water circulation and maintenance system for an ultrasound breast scanning apparatus. Referring now to FIGS. 1 and 2, principal components of the system are contained in a scanning tank cabinet 10 which encloses an untrasound system including a transducer tank 12 in which a scanning transducer 14 and associated sonic lens 16 are submerged in water. Transducer tank 12 has associated with it a transducer tank reservoir 18 in which a smaller quantity of water is maintained in filtered, purified, deaerated, and heated condition available to supply the proper level of substantially interference-free transmission medium for the scanning transducer tank 12. A motor coupled to a threaded shaft moves transducer tank 12 and its contents on a wheeled carriage along rails 102; as shown in FIG. 2.

Figure 1A:
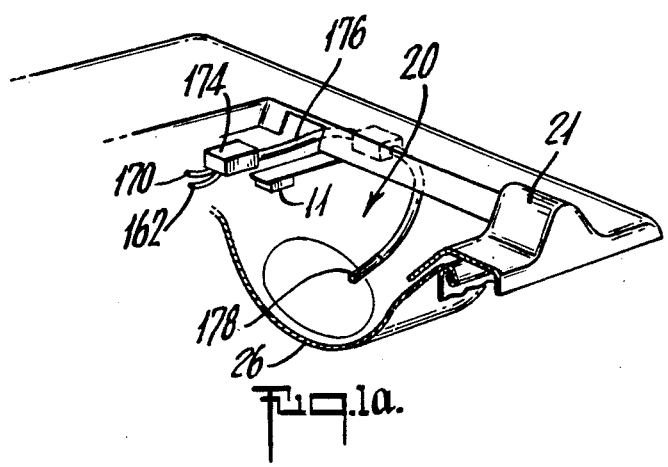
FIG. 1a shows a detailed perspective view of part of the invention.

Referring now to FIG. 1a, the top of cabinet 10 includes an aperture 20 oriented above scanning tank 12, through which aperture 20, the patient's breast may be suspended for examination by the ultrasound system within scanning tank 12. As shown in FIG. 2, fixed over a portion of the top of cabinet 10 is a rigid splash tray 22 with a well 24 aligned with aperture 20. A flexible membrane, or bag 26, is supported about the well by means of a frame 28 mounted in splash tray 22. The bag contains a pool of water 23 in which the patient's breast may be suspended during diagnosis. Bag 26 is designed so that it drapes down from support frame 28 and contacts the surface of the water in transducer tank 12 so as to provide a continuous transmission medium through which the ultrasound may be propagated from transducer tank 12 to suspension pool 23. Bag 26 forms an interface 25 between the water in transducer tank 12 and pool 23 isolating one from the other. An Imaging apparatus may be directed at the region under diagnosis via a viewing aperture, as shown in FIG. 2.

The present water circulation and maintenance system includes two separate but interdependent systems. One recirculation system is provided for the water in bag suspension pool 23 and a second recirculation system is provided for the water in the transducer tank 12. Each system has its own reservoir, filter, pump, heater, bacteria growth inhibitor and water level monitor so that the water may be maintained in condition to act as a good transmission medium for the ultrasound waves.

The principal parts of each circulation system will now be identified in connection with FIGS. 1 and 2. The method of filling, emptying and operating the systems will then be described in connection with FIGS. 3 and 4.

Circulation Systems Components

Main transducer tank 12 has a main reservoir 18 mounted on a shelf inside cabinet 10. A filter 42 for filtering undissolved particulate contaminants is mounted in main reservoir 18. A circulation pump 44 for the main tank 12 and its reservoir 18 is mounted within cabinet 10 beneath main reservoir 18. Filter 42 is preferably mounted within reservoir 18 to make it easier to control the temperature of the water as it passes through the filter. However, filter 42 could be located outside reservoir 18. A heater 46 for maintaining the temperature of the water in the main tank circulation system at the proper level is mounted within cabinet 10. A temperature sensor 154 is mounted in reservoir 18 to monitor the temperature of the water therein and operate heater 46. It is important to eliminate thermal gradients from the water in tank 12, because they can interfere with the ultrasound transmissions. A float valve 48 is mounted within main tank reservoir 18 for maintaining the proper level in the main tank reservoir 18. The construction and operation of float valve 48 will be discussed in detail in connection with FIGS. 4 and 5.

A separate reservoir tank 50 for the suspension pool 23 is also mounted in cabinet 10 on a shelf beside main reservoir tank 18. Suspension pool reservoir tank 50 is fitted with a filter 52, pump 54, heater 56, temperature sensor 166 and float valve 58, all of which are similar to and mounted in a similar fashion to the corresponding items for the main tank reservoir 18.

Main reservoir 18 and bag reservoir 50 each have an electrically operated valve 49 and 59 (see FIG. 4), respectively, which respond to a signal generated by float valves 48 and 58, respectively, to maintain the water level in reservoirs 18 and 50 at the proper level.

These components of the main tank circulation system and the bag suspension pool circulation system are connected by suitable water conduits and have associated manual and automatic valves for controlling and directing the flow, as will be described in greater detail in connection with FIG. 4.

The circulation system also includes a main discharge pump 60 which is used to empty bag suspension pool 23 and for emptying the main tank 12, as will be described in connection with FIG. 4.

A chlorination system 70, may be included to inject metered amounts of chlorine into the main reservoir 18 and bag reservoir 50 to circulate through these respective systems for controlling bacteria growth.

The system may also include a de-bubbler 80 for removing bubbles from main tank 12, particularly from under the concave surface of focusing lens 16 under which surface bubbles can be easily trapped and interfere with the ultrasound transmissions. A tube 82, situated underneath focusing lens 16 of transducer 14, provides a conduit for channelling water out of the main holding tank into an oscillating pump mounted inside the cabinet 10. A second tube 84 channels the main tank water from de-bubbler 80 into the main reservoir 18 where bubbles escape to the open surface of reservoir 18.

De-bubbler 80 is particularly useful if lens 16 is stationary in tank 12, but it may be omitted if lens 16 moves in tank 12 with transducer 14, because the motion will substantially reduce the ability of bubbles to become trapped under the lens.

Referring now to FIG. 3, there is shown a thermostatic water mixing assembly 90 which provides the interface between the external water source at the facility where the scanning apparatus is installed and the scanning tank unit. Mixing assembly 90 permits water pressure and boiler water available at the facility where the unit is installed to be used in the water circulation systems. Thermostatic water mixing assembly 90 is enclosed in a separate housing 92 from cabinet 10 which may be placed on the floor near cabinet 10. In one mode of operation, thermostatic mixing assembly 90 is used to provide ordinary tap water for filling main tank 12 and its associated reservoir 18 and bag reservoir 50. In a second mode of operation, thermostatic mixing assembly 90 is used to provide temperature-controlled water directly to suspension pool 23. As will be described subsequently in greater detail, the ability to fill suspension pool 23 directly with temperature-controlled water from the facility boilers facilitates the changing of the water in suspension pool 23 periodically as different patients are examined with the apparatus. The use of the two independent circulation systems permits the water in suspension pool 23 to be periodically changed for aesthetic and sanitary reasons without having to change the much larger quantity of water in the remaining part of the system. Thus, a large volume of new water does not have to be completely reconditioned by filtering, deaerating, heating and chlorinating each time a new patient uses the machine.

Still referring to FIG. 3, there is shown the internal structure of thermostatic mixing assembly 90. Incoming fittings 94 and 96 are connected respectively to the cold-water and hot-water piping at the facility where the scanning unit is installed. A dump water fitting 98 and an auxiliary drain fitting 100 are also provided in housing 92.

Cold water inlet 94 extends directly through housing 92 to outlet 104 which is connected to the reservoir feed of the conduits in cabinet 10 as will be discussed further in connection with FIG. 4. Hot-water inlet connection 96 is connected to mixing valve 106. The incoming cold-water conduit 94 is also connected to mixing valve 106 through branch 108. A second branch 110 arises from mixing valve 106 and splits at T-joint 112, with one arm of "T" 112 directed to dump-water fitting 98 and the other arm of "T" 112 directed to outlet bag feed connection 114. A first temperature sensor 116 is located at T-joint 112 and is electrically connected to junction box 118. A second temperature sensor 120 is located in the water conduit between T-joint 112 and outlet bag feed 114 for sensing whether the temperature being feed to the bag exceeds a predetermined maximum temperature, for example 115° F., and is also electrically connected to junction box 118.

A manual shut-off valve 124 is provided in incoming cold-water line 94 downstream of branch 108. A first electrically operated solenoid valve 126 is provided in branch 110, downstream of mixing valve 106 and is electrically connected into junction box 118 and is responsive to the temperature sensed by maximum temperature sensor 120. If the temperature of the water being feed to the outlet bag feed 114 exceeds 115° F., temperature sensor 120 generates a signal which shuts off solenoid valve 126 and also turns on a light on the control panel to signal the operator that the water being fed to bag suspension pool 23 is too hot for the comfort of the patient. The operator then adjusts mixing valve 106 accordingly. The mixing valve is a rotary valve, and turning handle 128 of mixing valve 106 clockwise decreases the temperature. Turning handle 128 counterclockwise increases the temperature.

An electrically operated solenoid valve 130 is provided in the conduit between T-joint 112 and dump-water drain 98. Another electrically operated solenoid valve 132 is provided in the conduit between T-joint 112 and outlet bag feed 114. Temperature sensor 116 monitors the temperature of the water at T-joint 112. If the temperature is below 100° F. and thus is too cold to be comfortable for a patient, temperature sensor 116 generates a signal which closes valve 132 and opens valve 130 to dump the flow of water from mixing valve 106 to dump-water fitting 98 and into a drain provided at the facility where the scanning unit is installed. When the water rises to a temperature of 100° F., temperature sensor 116 generates a signal which closes valve 130 and opens valve 132 to direct water at the correct 100° F. temperature to suspension pool 23.

The appropriate electrical connections between temperature sensors 116, 120 and solenoid valves 126, 130 and 132 are provided in junction box 118. A source of AC power is also connected into junction box 118 through a conventional electrical plug 134, which may be plugged into the electrical system available at the facility where the scanning unit is in use.

An auxiliary drain fitting 136 is also provided on the outlet side of housing 92. As will be explained more fully in connection with FIG. 4, auxiliary drain 136 provides a method for removing overflow water from the system.

Referring now to FIG. 4, the two separate but interdependent water circulation systems for the scanning unit will now be described. First the method for filling and emptying reservoir 18, tank 12, reservoir 50 and suspension pool 23 will be described, then the circulation of water through the operational systems will be described.

Filling and Emptying the System

The thermal mixing assembly 90 is connected to the water system at the facility where the scanning unit is installed by connecting cold water inlet 94 to the source of cold water and hot water inlet 96 to the source of hot water and by connecting dump water drain 98 and auxiliary drain 100 to a sink or floor drain provided at the facility. The reservoir feed 104 and bag feed 114 and auxiliary drain 136 are appropriately connected to the corresponding fittings provided on cabinet 10. The electric plug 134 is connected to the power provided at the facility. Additional electrical power is connected to the electrical elements within cabinet 10 so that the solenoid valves, float switches and other electrical components may be properly operated.

It is first necessary to fill the main tank reservoir 18 and main tank 12 because bag 26 containing suspension pool 23 rests on the top of the water in main tank 12 and obtains support therefrom. Manual valve 124 and incoming cold water line 94 is opened. A button on control panel located on the back of cabinet 10 on control panel 15 as shown in FIG. 1 is activated to open electrical fill valve 49 for main reservoir 8. Water flows through reservoir feed 104 to main reservoir 18 until float valve 48 shuts off fill valve 49. At the same time, float valve 48 sends a signal to main tank circulation pump 44 and water circulates from main reservoir 18 to the main tank 12. As the water level in main reservoir 18 drops, float switch 48 will again open fill valve 49.

When main tank 12 and its associated reservoir 18 are filled, the operator activates a second switch on control panel 15 to open fill valve 59 and direct tap water from reservoir feed 104 through fill valve 59 to inlet 160 of bag reservoir 50 until float valve 58 activates and sends a signal shutting off fill valve 59. Circulation pump 54 is not activated by the float valve 58. In this respect, the filling of the bag circulation system is different from the filling of the main tank circulation system. The suspension pool is not filled with cold water directed through reservoir 50, but is directly filled with temperature-controlled water from thermal mixing assembly 90 using facility boiler water. This permits the water in suspension pool 23 to be changed frequently without having to change the larger volume of water in the rest of the system.

To fill bag 26, the operator pushes a fill button on the control panel 15 to fill the bag 26 with water from thermal mixing assembly 90. Thermal mixing valve 106 is adjusted to let hot water enter through incoming hot water conduit 96 and cold water enter through incoming cold water conduit 94 and branch 108. The fill button also opens solenoid valve 126 and permits water to flow up to T-joint 112, where its temperature is sensed by temperature sensor 116. If the temperature is below the desired temperature of approximately 100° F., temperature sensor 116 opens solenoid valve 130 and closes solenoid valve 132 to dump the low temperature water through dump water drain 98. As soon as the temperature of the water at T-joint 112 reaches the desired temperature, temperature sensor 116 closes valve 130 and opens solenoid valve 132 to permit water at the correct temperature to exit thermal mixing assembly 90 through bag feed connection 114 and into bag inlet 170 through manifold 174, filling pipe 176, and curved terminal portion 178 into the bag (see FIG. 1A). Bag inlet 170 is contained in the manifold 174 mounted within the trough of splash tray 22. A filler pipe 176 extends from manifold 174 through top cover 21 and extends to a curved terminal section 178 which extends below the surface of the water in suspension pool.

The bag 26 continues to fill until a float switch 11, mounted under top cover 21 and projecting into suspension pool 23, senses that the level of the water in bag 26 has reached its desired level and sends a signal to solenoid valve 126 shutting off the flow of temperature controlled water from thermal mixing assembly 90. The signal from float switch 11 also activates circulation pump 54 for the bag circulation system so that water begins to circulate through the bag circulation system.

The emptying of the system can be accomplished as follows. Bag 26 must be emptied before main tank 12 because bag 26 rests on the surface of the water in main tank 12. Valve 62 is closed and discharge pump 60 is turned on by activating a switch on control panel 15. Closing valve 62 prevents pump 60 from draining the main tank. Discharge pump 60 then draws water from inlet 170 in manifold 174 out through curved terminal portion 178 of filler pipe 176 until the bag is substantially empty. Bag reservoir 50 may then be emptied by continuing to operate circulation pump 54 and circulating the contents of bag reservoir 50 into bag 26 where it is emptied by discharge pump 60 in the same fashion as previously described. In order to accomplish this result, float valve 58 must be deactivated so that it will not send a signal to open fill valve 59 and draw additional water into bag reservoir 50.

To empty main tank 12, valve 62 is opened so that discharge pump 60 will draw water from outlet 172 of main tank 12 to drain 140. Curved terminal portion 178 of filler pipe 176 is covered while main tank 12 is being emptied so that pump 60 does not draw entrained air through terminal portion 178, outlet 170 and into the pump 60. This entrained air would substantially reduce the flow rate of water from tank 12. After tank 12 is emptied, water from main reservoir 18 is emptied by operating circulation pump 44 and taking water from main reservoir 18 through outlet 146 through the circulation system into main tank inlet 148. Float valve 48 must be deactivated so that it will not send a signal opening fill valve 49.

In this way the system can be emptied. Alternatively only bag 26 need be emptied and then refilled, for example, after each patient or every few patients. Since the water enters bag 26 at the desired temperature, only a short circulation time is required to remove particulate matter, add purifying chlorine and deaerate the bag water.

Circulation System

The circulation of water through the two independent systems for tank 12 and bag 26 will now be discussed in connection with FIG. 4.

It is necessary to circulate water through the two systems so that the water in tank 12 and bag 26 is maintained in the proper condition to function as a substantially continuous transmission medium for the ultrasound waves from transducer 14 to the patient's breast. Water must be circulated to remove entrained air which can interfere with the breast scan image. The level of water in each system must be maintained so that the water in bag 26 is close to the patient so the entire breast and surrounding axillary region may be easily submerged. The level of the water in tank 12 must be maintained so that bag 26 may rest against the surface of the water in tank 12 without gaps which would cause the ultrasound transmissions to refract. Uniform temperature must be maintained to eliminate thermal gradients which could interfere with the image. Particulate matter must be removed and bacteria growth must be inhibited for the same reason. The present system achieves all of these goals and provides a dual circulation system which permits bag water to be changed frequently without the need for changing and conditioning the large volume of water in the remainder of the system. When the main tank system is filled, water is circulated under the influence of pump 44 through outlet 146 of main tank reservoir 18 to main tank circulation pump 44, where it is pumped through particulate filter 42 located in main tank reservoir 18, from which the water circulates further to main tank circulation system heater 46 and thence to the inlet 148 of main tank 12. A skim pipe 150 skims water from the top of main tank 12 back to inlet 152 of main tank reservoir 18. The water level in main tank 12 is above that of the water level in main tank reservoir 18 so that the water is returned from skim pipe 150 to inlet 152 by a gravity return.

The bag circulation system operates similarly to the main tank circulation system. Water is circulated from bag reservoir outlet 162 through circulation pump 54 to filter 52 located within bag reservoir 50. Water is circulated further to heater 56 and thence to the inlet 164 of bag reservoir.

Water is allowed to spill over the edge of bag support frame 28 into splash tray 22, as shown in FIG. 2, and back through drain 171 to bag reservoir inlet 168 to complete the circulation system for the bag. Since splash tray is above the level of reservoir 50, the return is a gravity return.

It is important to permit the water to circulate through the two respective systems for a period of time of about one hour prior to its first use so that the water in the system can be completely deaerated. Air bubbles in main tank 12 and in bag 26 may interfere with the ultrasound transmissions and distort the ultrasound image. The surface of the water in bag reservoir 50 and main reservoir 18 is open so that each circulating system is an open system. As circulation pumps 44 and 54 drive water through the system any entrained air bubbles are allowed to escape from the surface of the two reservoirs. Thus, after circulating the water in the two circulation systems for a period of time, the water is substantially deaerated.

The main tank circulation system also includes a de-bubbling pump apparatus 80, mounted within cabinet 10. A de-bubbler drain tube 82 takes water from under the concave surface of sonic focusing lens 16 and directs it to a de-bubbling pump 81 and thence to inlet 156 of main tank reservoir 18 where the water is then circulated through the main tank circulating system as described above. The de-bubbling pump is a commercially available pump which can be purchased from Gorman-Rupp Company of Belville, Ohio 44813, pump Model No. 14825-003. Alternatively, lens 16 may be adapted to move with the scanning transducer as it moves across tank 12 during the scanning operation. The motion of lens 16 creates a water flow under the lens so that bubbles are not likely to be trapped under the concave surface of the lens.

After the systems are filled, the mode of operation of valves 49 or 59 is switched to the circulation mode where it is responsive to the float valves 48 or 58, respectively. When, for example, the water level in main reservoir 18 falls below a predetermined level, float valve 48 will open fill valve 49 and permit water to flow into main reservoir 18 until float valve 48 indicates that the proper water level has been restored, at which time float valve 48 generates a signal to close fill valve 49. Fill valve 59 for the bag reservoir operates in the same way, responsive to the operation of float valve 58 in bag reservoir 50. Bag 26 requires replenishing after every patient because as the patient's breast is introduced into suspension pool 23, a certain amount of overflow occurs because the water level is maintained close to the brim of the bag support frame 28. This spillage runs into splash tray 22 through drain 171 back to bag reservoir 50. Overflow tube 55 in bag reservoir 50 provides a means for draining any excess water from bag reservoir 50 out through auxiliary drain 136. When the breast is withdrawn, the water level recedes so that the water may not totally submerge the breast and surrounding axilla region of the next patient unless more water is added. If a large amount of water must be added, it can be introduced from thermal mixing assembly 90. If only a small amount is needed, it can be introduced from reservoir 50 and float valve 58 will respond to the decreased water level to open fill valve 59. Thus, the water level is constantly monitored and water replenished as needed.

Water can also be lost from tank 12, bag 26 or reservoirs 18 and 50 through evaporation. Float valves 48 and 58 will respond to this need by opening fill valve 49 or 50 as appropriate.

Temperature sensors 154 and 166, located respectively within reservoirs 18 and bag reservoir 50, monitor the temperature of the water in reservoirs 18 and 50. Continuous circulation maintains uniform temperature and substantially eliminates undesirable thermal gradients. If the water temperature falls below a predetermined level, preferably 100° F., temperature sensors 154 or 166 will turn on main tank circulation system heat 46 or 56 to raise the temperature to the desired level. Heaters 46 and 56, for the main tank circulation system and the bag circulation system respectively, are deliberately chosen to have a small wattage (about 350 watts each) to keep the amperage requirement of the system unit as low as possible. Each heater is large enough to maintain the temperature at the desired temperature level of about 100° F., but if the system is initially filled with water substantially below 100° F. in temperature, several hours are required for the two heaters to bring the water volume up to 100° F. For this reason, it is desirable that the water for suspension pool 23 come from separate thermostatic mixing assembly 90, rather than from a cold water tap. Using thermostatic mixing assembly 90 permits boiler water at the facility where the scanning unit is installed to provide the thermal energy for the water charge for suspension pool 23. This permits the bag water to be changed periodically, for example, after each individual patient or at least after each several patients, without having to heat the larger volume of water maintained in the two reservoirs 18 and 50, and in the main tank. These two heaters 46 and 56 are standard commercial units available, for example from Watlow Company of 12001 Lackland Road, St. Louis, Mo. 63141, heater Model No. L3JX69A.

It is important to have the water in bag 26 at a comfortable 100° F. temperature so that the patient will not experience discomfort when the patient's breast is inserted into the water in the bag. Although the water in main tank 12 is physically isolated by bag 26 from the water in the suspension pool so that it would not affect patient comfort, it is necessary to maintain the temperature of the water in main tank 12 at about the same level as the water in bag 26 so that the transmission medium for the ultrasound transmissions from transducer 14 through sonic lens 16 will not experience any distortions at the interface between water in main tank 12 and bag 26. If the temperature of these two bodies of water is different or if the thermal gradients are present, the transmission of the ultrasound may be detrimentally affected so that the resulting breast image may not provide the desired results. For the same reason, the bag is chosen of a material which is substantially ultrasonically transparent so that the bag itself in addition to the interface between the water in tank 12 and bag 26 will not have any effect on the transmission of the ultrasound energy.

It is also necessary to remove particulate matter which may interfere with the ultrasound transmission. As water skims off the top of main tank 12, through skim pipe 150, floating particulate matter is drawn off and circulated back through filters 42. Continuous circulation of the water, therefore, facilitates the continuous removal of particulate material to remove undissolved contaminants which can interfere with ultrasound transmission and make the water appear dirty. Water that spills out of bag 26 over the edge of frame 28 also carries particulate matter with it back to filter 52 for removal. Filters 42 and 52 are commercially available filters which may be purchased from Carborundum Co., Filter Division, Lebanon, Ind. 46052, FUL-FLO* heater Model No. F15-10.

The water circulating systems for main tank 12 and for suspension pool 23 are also provided with a chlorination system 70 for controlling bacteria growth within the reservoirs 18 and 50, main tank 12 and suspension pool 23. The present chlorination system includes a bottle 72 mounted within the scanning cabinet 10, containing a chlorine solution. The bottle is preferably a 2 liter bottle, and the solution is preferably a 10% chlorine solution. The bottle has two outlets 74 and 76 which are connected to a chlorine pump unit by pieces of separate flexible tubing 182 and 184. Tubing 182 and 184 leads through separate peristaltic pumps (not shown) which operate in response to signals generated by chlorine concentration sensors 186 and 188, located respectively in main reservoir 18 and bag reservoir 50. The chlorine concentration sensors are preferably a platinum redox chlorine sensor of the kind manufactured by Chemtrol Corporation of California. When the chlorine level drops below a desired concentration, chlorine sensors 186 and 188 or both generate a signal to turn on either one of the pumps in chlorine unit 78 which operate to deliver a measured amount of chlorine solution from chlorine bottle 72 through the pumps (not shown) to outlets 190 and or 192 of chlorine dispensing unit 78 through appropriate tubing to inlet 194 of main reservoir 18 or inlet 196 of bag reservoir 50. Thus, the water in the respective reservoirs is properly chlorinated, and the chlorinated water can be circulated through the independent systems as discussed above.

Each reservoir has an overflow to prevent the water level from getting too high and spilling over the edges of the reservoirs. The overflow includes a hollow tube 45 extending through connection block 47 and connected to a drain 136 through an ordinary gravity flow. Hollow tube 45 acts as a stand pipe and when the water level rises above its open end, the water flows down through the tube and out to drain 136. A similar tube 55 and connecting block 57 are provided in bag reservoir 50 and is connected in parallel with tube 45 to drain 136.

A manual shut-off valve 43 is provided downstream of heater 46 and a corresponding manual shut-off valve 53 is provided downstream of heater 56. The shut off valves are provided so that heaters 46 or 56 may be replaced without having to drain water from the entire system. The valve is placed at a height which is greater than the height of the water level in either main reservoir 18 or bag reservoir 50 so that when heater 46 or 56 is disconnected only the water in the connection between outlet 146 or 168, respectively, and heater 46 or 56 will drain. Without shut off valve 43 or 53 water from the main tank 12 or from bag 26 could flow back from their respective inlets 148 or 164 and permit at least a portion of the main tank 12 and or bag 26 to drain.

A check valve 180 is also provided between bag inlet 164 and heater 56 to prevent water from draining from bag 26 if pump 54 fails or power is lost. This is necessary because bag 26 is higher than bag reservoir 50, and if pump 54 stopped, gravity would drain bag 26 back to reservoir 50 and out overflow pipe 55.

Referring now to FIG. 5, there is shown an elevation, partly in section, of the float valve 48 and 58 used to maintain the proper level of water in main reservoir 18 and bag reservoir 50.

Float valve 48 includes a hollow stem 200 threaded into a connecting block 202 which passes through the bottom of main reservoir 18. The top of hollow stem 200 flares into a generally cylindrically shaped cup 204 which is open at the top. The bottom of cup 204 has a weep hole 206. Threaded into the top of hollow stem 200 and extending into the interior of cup 204 is a hollow slider 208 having a washer-shaped metal stop 210 connected around its top. Float 212 slides up and down on slider 208 according to the water level in cup 204. Stop 210 limits the upward travel of float 212. A magnetically actuated switch 207 is hermetically sealed within hollow slider 208 and is connected to electrical wire 214 which lead out through hollow stem 200. Permanent magnets 209 are mounted in float 212 and are enclosed in plastic to isolate them from the surrounding water. When the float moves down from stop 210, it reaches a critical point where the magnetic field created by magnets 209 will actuate and close switch 207. Electrical contacts 214 for float valve 48 are electrically connected to electrically operated fill valve 49 for the main reservoir and corresponding float valve 58 is electrically connected to fill valve 59 for the bag reservoir. Electrical connection is also provided between contacts 214 of main reservoir float valve 48 and circulation heater 46 so that when the water level drops, the heater is shut off to prevent electrical damage to the heater. Corresponding electrical connections are provided between the bag reservoir float valve 58 and its heater 56 for the same reason.

Float valve 48 operates as follows. As main reservoir 18 fills, water enters cup 204 through weep hole 206 and also spills over the top of cup 204 and fills cup 204.

Float 212 then slides up on slider 208 rises past the critical point where the magnetic field from magnets 209 releases switch 207 so that it opens and shuts off valve 49. Stop 210 limits the upward travel of float 212. If the water level in main reservoir 18 drops below the level of weep hole 206, through for example evaporation, the water in cup 204 will flow out through weep hole 206. Thus the water level in cup 204 will drop, and float 212 will slide down slider 208 away from stop 210 thus permitting magnets 209 to close switch 207 and generate a signal for opening fill valve 46 to permit water to flow into main reservoir 18 and again raise the water to its desired level in main reservoir 18. Also, when the water level drops in main tank 18, a signal is sent from float valve 48 to prevent heater 46 from turning on. Once the water level in main tank 18 rises to its desired level, float valve 48 sends a signal to heater 46 which returns it to the operating condition so that the heater can turn on if the temperature of the water in the main reservoir circulation system so requires. Thus, even if the water which is used to refill main reservoir 18 is very cold and temperature sensor 154 generates a signal to turn on heater 46, the over ride signal from float valve 48 will not permit heater 46 to turn on until the water has reached its desired level. Thus, it can be seen that the water level in the reservoirs 18 and 50 is maintained at the proper level through the operation of float valves 48 and 58.

It will be appreciated that the present invention provides a circulation system for the scanning unit which includes two separate but interdependent water circulation systems for pumping, filtering, heating, deaerating and purifying the water in the systems. The present invention has been described in conjunction with the preferred embodiments. Those skilled in the art will appreciate that many modifications and changes may be made to the preferred embodiments without departing from the present invention. It is, therefore, not intended to limit the present invention except as set forth in the appended claims.

We claim:

1. Apparatus for conditioning a fluid transmission medium for an ultrasound imaging system used for examining a patient's breast, said apparatus comprising transducer means for transmitting to and receiving sonic energy from the patient,:
   a main tank enclosing a first quantity of transmission medium and adapted to house an ultrasound transducer and associated focusing lens, and having an open top facing said patient;
   a main reservoir in fluid communication with said main tank;
   a main circulation circuit for circulating said fluid transmission medium between said main tank and said main reservoir and for conditioning the medium therein to facilitate the transmission of the ultrasound;
   a suspension pool of transmission medium isolated from fluid communication with said main tank and adapted to receive a patient's breast;
   a suspension pool reservoir in fluid communication with suspension pool; and,
   a suspension pool circulation circuit for circulating said medium between said suspension pool and said suspension pool reservoir and for conditioning the medium therein to provide a substantially continuous fluid transmission medium from transducer through said main tank and through said suspension pool to the patient.

2. The apparatus of claim 1 wherein said main circulation circuit includes:
   filtration means for removing particulate matter from said medium;
   temperature control means for regulating the temperature of said medium;
   means for maintaining the level of the medium in said tank at the desired level; and,
   pumping means for circulating said medium through said main circuit for facilitating the filtration, temperature control and level maintenance of said medium in said main circuit.

3. The apparatus of claim 2 further including:
   a skim pipe in said main tank disposed at a level higher than the level of the water in said main tank reservoir for providing a gravity feed return for said main tank circulation circuit from said main tank to said main tank reservoir;
   said skim pipe facilitating the removal of particulate matter from said main tank so that it may be circulated through said main tank circulation circuit filter means.

4. The apparatus of claim 1 wherein said suspension pool circulation circuit includes:
   filtration means for removing particulate matter from said medium;
   temperature control means for regulating the temperature of said medium;
   means for maintaining the level of the medium in said suspension pool at the desired level; and,
   pumping means for circulating the medium through said suspension pool circulation circuit for facilitating the filtration, temperature control and level maintenance of said medium in said suspension pool circuit.

5. The apparatus of claim 4 wherein said suspension pool is disposed at a level higher than said pool reservoir and further including:
   backflow prevention means to prevent fluid from flowing from said pool to said pool reservoir in the event that said suspension pool circulation circuit pumping means stops while fluid is in said pool.

6. The apparatus of claim 2 or 4 wherein said main circuit filtration means is disposed within said main reservoir.

7. The apparatus of claim 2 or 4 wherein said temperature control means includes a temperature sensor disposed in said reservoir and a heater operatively associated with said temperature sensor for regulating the temperature of said medium in said circulation circuit.

8. The apparatus of claim 2 or 4 wherein said level maintaining means includes a float switch disposed in said reservoir and a fill valve operatively associated with said float switch and adapted to introduce additional medium to said reservoir when the level in said main tank, said reservoir or said suspension pool falls below a predetermined level.

9. The apparatus of claim 8 further including override means associated with said float switch for shutting off said temperature-control means when the level of said medium in said main circulation circuit drops below a desired level to thereby protect said temperature control means against damage from over heating.

10. The apparatus of claim 2 or 4 wherein the fluid in said main reservoir is exposed to the atmosphere so that as transmission medium circulates through said circulation circuit under the influence of said pumping means, air in said medium may be purged therefrom by escaping as bubbles at said reservoir open surface.

11. The apparatus of claim 1 wherein said main circulation circuit further includes:
de-bubbling means for removing bubbles which may be trapped under said sonic lens.

12. The apparatus of claim 1 further including a flexible bag means having an open end supported adjacent said patient and having a closed end draped into engagement with the medium in said main tank;
said bag means adapted to contain said suspension pool and forming an interface between the fluid in said pool and in said tank;
the transmission properties of the fluid in said tank and in said pool and of said bag means permitting transmission of sonic waves from said transducer therethrough without substantial distortion of said sonic energy.

13. The apparatus of claim 12 further including a splash tray disposed about the open end of said bag means;
and wherein the level of the fluid in said suspension pool is above the level of the fluid in said suspension pool reservoir;
the fluid in said suspension pool being permitted to run over the edge of said bag means into said splash tray and to return to said suspension pool reservoir under the influence of gravity, said suspension pool overflow carrying with it particulate matter for return to said suspension pool reservoir for removal by said suspension pool circulating circuit.

14. The apparatus of claim 2 wherein said main circulation circuit further includes means for controlling the growth of bacteria in said main tank.

15. The apparatus of claim 4 wherein said suspension pool circulation circuit further includes means for inhibiting the growth of bacteria in said suspension pool.

16. The apparatus of claims 14 or 15 wherein said bacteria growth inhibiting means includes;
a reservoir containing a chlorine solution;
separate bacteria growth inhibitor sensors disposed in said main reservoir and in said pool reservoir; and
means for dispensing measured amounts of chlorine from said chlorine reservoir to said main reservoir or said bag reservoir in response to said bacteria growth inhibitor sensor.

17. The apparatus of claim 1 wherein said fluid medium is water and further including a thermostatic mixing assembly providing fluid communication between the water supply at the facility where said patient is being examined and said conditioning apparatus;
said thermostatic mixing assembly operative in a first mode for selectably filling said main circuit or said suspension pool reservoir with water; and,
said thermostatic mixing assembly operative in a second mode for filling said suspension pool with water at a controlled temperature to thereby facilitate the frequent changing of the water in said suspension pool without necessitating changing of the water in said main tank circulation circuit or in said suspension pool reservoir.

18. The apparatus of claim 17 wherein said thermostatic mixing assembly includes:
an incoming hot water conduit;
an incoming cold water conduit;
a reservoir feed in fluid communication between said incoming cold water conduit and said main tank reservoir and said suspension pool reservoir;
a mixing valve having input ports respectively in fluid communication with said incoming hot water conduit and said incoming cold water conduit and having an outlet port in fluid communication with a T-junction;
a dump-water drain in fluid communication with said T-junction;
a suspension pool feed in fluid communication between said T-junction and said suspension pool;
first and second valve means disposed respectively between said dump water connection and said T-junction and said suspension pool feed and said T-junction;
temperature sensor means for sensing the temperature at said T-junction and operatively associated with said first and second valve means in a first mode to provide fluid communication between said dump water connection and said T-junction and to block said fluid communication between said T-junction and said suspension pool feed if the water from the outlet port of said mixing valve is below a desired temperature level;
said temperature sensor operatively associated with said first and second valve means in a second mode to provide fluid communication between said T-junction and said suspension pool feed and to block fluid communication between said dump water connection and said T-junction if the temperature of the water leaving said outlet port of said mixing valve is at a desired temperature level.

19. The apparatus of claim 18 further including:
third valve means between said mixing valve outlet port and said T-junction;
a second temperature sensor means for monitoring the temperature of the water between said T-junction and said suspension pool feed and operative by associated with said third valve means to block fluid communication to said suspension pool feed if the temperature of the water delivered thereto exceeds a predetermined level.

20. The apparatus of claim 1 further including:
a discharge pump;
valve means for selectively providing fluid communication between said discharge pump and said main tank or said suspension pool;
said pump adapted for draining said pool or said pool and said tank according to the setting of said valve means.

21. The apparatus of claim 1 further including overflow means disposed in each of said reservoirs to prevent said reservoirs from overflowing.

22. Apparatus for conditioning a fluid transmission medium for an ultrasound imaging system used for examining for examining a patient's breast, said apparatus comprising transducer means for transmitting to and receiving sonic energy from the patient:
a main tank enclosing a first quantity of transmission medium and adapted to house an ultrasound transducer and an associated focusing lens;
a suspension pool of transmission medium interfacing with but isolated from fluid communication with the fluid in said main tank and adapted to receive a patient's breast;
separate reservoirs for said main tank and said pool;
separate circulation circuits respectively providing fluid communication between said main tank and said main tank reservoir and said pool and said pool reservoir for conditioning the medium therein to facilitate the transmission of the ultrasound energy from said transducer through the medium in said tank and in said pool to the patient without substantial distortion of said sonic energy.

* * * * *